United States Patent

Fearnot

(10) Patent No.: US 10,077,423 B2
(45) Date of Patent: Sep. 18, 2018

(54) COMPARTMENTED CRYOPRESERVATION CONTAINER AND USES THEREOF

(71) Applicant: Muffin Incorporated, West Lafayette, IN (US)

(72) Inventor: Neal E. Fearnot, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 0 days.

(21) Appl. No.: 14/614,491

(22) Filed: Feb. 5, 2015

(65) Prior Publication Data

US 2015/0216763 A1    Aug. 6, 2015

Related U.S. Application Data

(60) Provisional application No. 61/936,265, filed on Feb. 5, 2014.

(51) Int. Cl.
| | | |
|---|---|---|
| C12N 5/071 | (2010.01) | |
| B01L 7/00 | (2006.01) | |
| A01N 1/02 | (2006.01) | |

(52) U.S. Cl.
CPC ......... *C12N 5/0602* (2013.01); *A01N 1/0231* (2013.01); *A01N 1/0263* (2013.01); *B01L 7/50* (2013.01); *B01L 2300/069* (2013.01)

(58) Field of Classification Search
CPC .......... F17C 3/00; B65B 3/02; A01N 1/0263; A01N 1/0231; C12N 5/0602; B01L 7/50; B01L 2300/069
USPC ........................................ 220/560.08; 53/452
See application file for complete search history.

(56) References Cited

U.S. PATENT DOCUMENTS

| | | | | |
|---|---|---|---|---|
| 3,257,072 A | * | 6/1966 | Reynolds | A61M 1/029 137/255 |
| 5,638,686 A | | 6/1997 | Coelho et al. | |
| 6,206,931 B1 | * | 3/2001 | Cook | A61L 2/0088 523/113 |
| 7,770,611 B2 | * | 8/2010 | Houwaert | A61J 1/10 141/114 |

(Continued)

FOREIGN PATENT DOCUMENTS

| | | |
|---|---|---|
| JP | 09-276367 A | 10/1997 |
| JP | 2013-005825 A | 1/2013 |

(Continued)

OTHER PUBLICATIONS

Zou et al. Regeneration of mature dermis by transplanted particulate acellular dermal matrix in a rat model of skin defect wound. J Mater Sci: Mater Med (2012), v23, p. 2933-2944.*

(Continued)

*Primary Examiner* — Sean C Barron
(74) *Attorney, Agent, or Firm* — Woodard, Emhardt, Moriarty, McNett & Henry LLP

(57) ABSTRACT

Described are medical products, methods, and cryogenic bags or other containers suitable for storing and/or transporting and/or processing cellular compositions and other related materials. In certain aspects, the contents of such cryogenic bags may be warmed, mixed, and applied to a patient. Medical products described herein find particular use in treating diseased and/or damaged tissue such as in wound repair and/or bone repair. Related methods of manufacture are also described.

17 Claims, 2 Drawing Sheets

(56) References Cited

U.S. PATENT DOCUMENTS

| | | | |
|---|---|---|---|
| 2002/0168759 A1 | 11/2002 | Wang et al. | |
| 2003/0054331 A1 | 3/2003 | Fraser et al. | |
| 2008/0038231 A1* | 2/2008 | Rodgerson | A61K 35/28 424/93.7 |
| 2011/0022022 A1* | 1/2011 | Tsuruoka | A61J 1/10 604/410 |
| 2011/0250182 A1 | 10/2011 | Abbot et al. | |
| 2011/0309086 A1 | 12/2011 | Arnitz et al. | |
| 2013/0295673 A1 | 11/2013 | Taghizadeh et al. | |

FOREIGN PATENT DOCUMENTS

| | | |
|---|---|---|
| WO | WO 2000/06079 | 2/2000 |
| WO | WO 2000/18225 | 4/2000 |
| WO | WO 2004/093810 A2 | 11/2004 |
| WO | WO 2013/088262 A1 | 6/2013 |

OTHER PUBLICATIONS

Ma et al. Adipose tissue-derived stem cell-seeded small intestinal submucosa for tunica albuginea grafting and reconstruction. PNAS (2012), v109(6), p. 2090-2095 plus supporting information.*

Haas et al. Different populations and sources of human mesenchymal stem cells (MSC): A comparison of adult and neonatal tissue-derived MSC. Cell Communication and Signaling (2011), v9(12), 14 pages.*

"Cryopreservation and Freeze-Drying Protocols," Day, et al., 2nd ed PSBN 1-58829-377-7 2, 2007.

European Patent Application 15746191.4 Partial Supplementary European Search Report dated Oct. 17, 2017, 11 pages.

International Search Report and Written Opinion issued in PCT/US2015/014554, dated Apr. 13, 2015, 11 pgs.

European Patent Application No. 15746191.4 Extended Search Report dated Jan. 23, 2018. 10 pages.

* cited by examiner

US 10,077,423 B2

COMPARTMENTED CRYOPRESERVATION CONTAINER AND USES THEREOF

REFERENCE TO RELATED APPLICATION

This application claims the benefit of priority of U.S. Provisional Application Ser. No. 61/936,265, filed Feb. 5, 2014, which is hereby incorporated herein by reference in its entirety.

BACKGROUND

The present invention resides generally in the field of cryopreserved or cryopreservable medical products useful for convenient preparation of cellularized compositions.

As further background, a variety of cellularized compositions have been proposed for medical treatment. Such compositions often include cells and a porous matrix or other solid material for supporting or carrying the cells or otherwise contributing to the final composition. The combination of the cells and the solid material has been proposed at the point of care (e.g., bedside) in some instances, and in others cells are grown on a solid matrix, which is then administered to a patient.

Despite work to date in this area, needs exist for modes of and products for delivery of cellularized compositions to the health care marketplace which are both cost- and technologically-effective, as well as convenient. In certain of its aspects, the embodiments of the present disclosure are directed to these needs.

SUMMARY

In one aspect, provided is a cryogenic product useful for the preparation of a cellularized matrix composition. The product includes a cryogenic container defining a sealed internal volume. The cryogenic container includes a cellular composition and at least one additional, separate composition, preferably a solid material such as a porous matrix. The solid material can be in particulate form. The solid material and cellular composition can be contained within separate compartments within the cryogenic container, or in some embodiments can be contained within a single compartment or region of the container but provided as separate, non-mixable material volumes (e.g. a frozen mass of cellular composition and a mass (e.g. hydrated, frozen mass) of solid material, potentially particulate solid material.

In another aspect, a cryogenic bag defining a sealed internal volume provides one or more storage compartments for compositions where it may be advantageous to cryogenically store the compositions segregated from each other. In such an embodiment, segregation may be affected by, for example, storage in a separate storage compartment. Such a storage compartment can be integrally formed as a part of the cryogenic bag, such as a permanent compartment or sleeve, and/or can be a compartment formed (preferably reversibly formed) by a clamp or other compression element external of the bag that segregates one region of the bag from another.

In certain aspects, a cryogenically preserved cellular composition is received within a first compartment within the internal volume, and a porous matrix or other solid material is received within a second compartment within the internal volume. In preferred aspects, the first compartment and second compartment each define an opening to a third compartment within the sealed internal volume of the bag for mixing said cellular composition with said matrix composition. One or more compartments may be in fluid communication with one or more other compartments. In still another aspect, the one or more compartments, may be permanently and/or integrally formed by the cryogenic bag, and in other embodiments, may be transient, for example formed by a removable clamp or other compression element external of the bag.

In another aspect, provided is a method for preparing a cellularized matrix composition. The method involves thawing a cryogenic product as described immediately above or elsewhere herein, and causing admixture of the cellular composition, the solid (e.g. porous matrix) composition, and/or potentially other compositions within the cryogenic bag or other container. For example, in some embodiments, such causing of admixture can be accomplished by transferring the cellular composition and/or the matrix and/or other solid composition from a first compartment and a second compartment, respectively, to a third compartment, and mixing the cellular composition with the matrix or other solid composition in the third compartment to form a cellularized composition.

Additional aspects disclosed herein relate to methods for preparation of cryogenic products.

DETAILED DESCRIPTION

Figure 1:
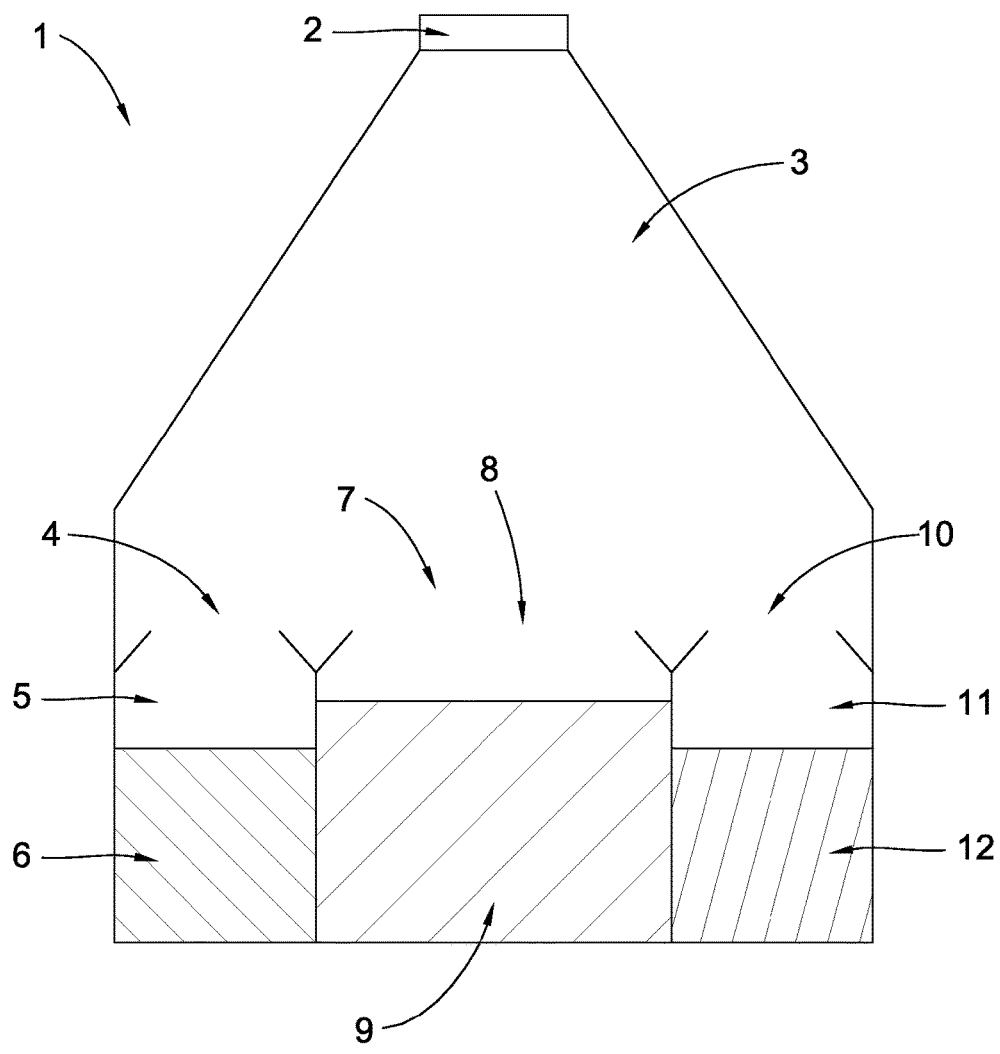
FIG. 1 is a plan view of one embodiment of the present disclosure.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device or devices, and further applications of the principles of the disclosure as illustrated therein are herein contemplated as would normally occur to one skilled in the art to which the disclosure relates.

As disclosed above, aspects of the present disclosure relate to novel methods and materials for treating diseased or damaged tissue in a patient. In certain aspects, the disclosure relates to materials comprising a solid material, for example a porous matrix material such as a particulate extracellular matrix (ECM) tissue, and cells. As will be discussed herein, a cryogenic bag or cryobag may be used to store such a solid material (e.g. ECM material), a cellular composition, and in some embodiments at least one additional material such as a liquid carrier, at low temperatures, including cryogenic temperatures for storage, transportation, and/or preparation. The cryogenic bag or other container may be employed to mix one or more compositions and/or apply a composition to a patient. In certain forms, the cryogenic bag or other container has at least one flexible wall capable of manipulation (e.g. physical kneading) to mix contents within the container.

Referring now to the figures, FIG. 1 shows a plan view of one embodiment of the present disclosure. In this embodiment, cryogenic bag generally designated 1, comprises a tag 2 that can be cut by surgical scissors, a mixing compartment 3, and storage compartments 5, 8, 11. Storage compartment 5 may comprise an opening 4, and a composition 6. Storage compartment 8 may comprise an opening 7, and a composition 9. Storage compartment 11 may comprise opening 10 and a composition 12. In one embodiment composition 6 comprises a carrier that is a liquid at room temperature and pressure. In one embodiment composition 9 may comprise a solid material, preferably a porous matrix composition, for example an ECM in particulate form. In one embodiment composition 12 may comprise cells, for example stem cells such as, but not limited to, mesenchymal stem cells. As can been seen from FIG. 1, storage compartments 5, 8, and 11 may be tapered as they lead to opening 4, 7, and 10 to facilitate flow-based transfer of compositions 6, 9, and/or 12 to mixing compartment 3 upon inversion of the bag. In this regard, it will be understood that in this embodiment and other embodiments described herein wherein compartments have openings that fluidly communicate with one another in a sealed internal volume of the bag and/or other container, the bag or other container may be stored (e.g. before and/or during cryogenic storage) in a position wherein the openings reside above the top surfaces of the respective contents of the compartments, thus using gravity to maintain the contents within their respective compartments. Storage compartments 5, 8 and 11 and storage compartments of other cryogenic bags or other containers herein may, in some embodiments, be formed integrally with the bag or other container. For example, this may be accomplished by welding or fusing opposed wall portions the pocket-forming materials (e.g. opposed walls of the container, or additional material pieces received within the container that are welded or fused to an interior portion of the container wall) along the boundaries of the compartments. In other embodiments, the compartments can be formed by one or more compression elements (e.g. clamps) external of the bag or other container that compress walls of the container against one another sufficiently to form seals to create the separate compartments (e.g. two, three or more compartments). Preferably these external compression elements are releasable from the bag or other container so as to eliminate the pockets. In this manner, in certain modes of use, the compression element(s) can be removed after the product is removed from cryogenic storage, so as to allow for mixing of the contents of the bag, e.g. to create cellularized compositions as discussed herein. In other modes of use, the compression elements may be removed after the materials within the bag or other container are frozen to discrete, non-mixable solid masses. Storage at cryogenic temperatures will then prevent mixing of the solid masses during the period of storage, and upon thawing the solid masses can be dispersed and mixed within one another to create a cellularized composition, e.g. any of those discussed herein. It will be understood that these integral or non-integral (e.g. external clamps or other compression elements) compartment-forming features can also be used in conjunction with all other cryostorage containers described herein.

The contents of compartments 5, 8 and/or 11 may be any of those materials disclosed herein, preferably including a cellular composition, a solids composition, and in some embodiments also a carrier composition, separately stored as described herein.

Figure 2:
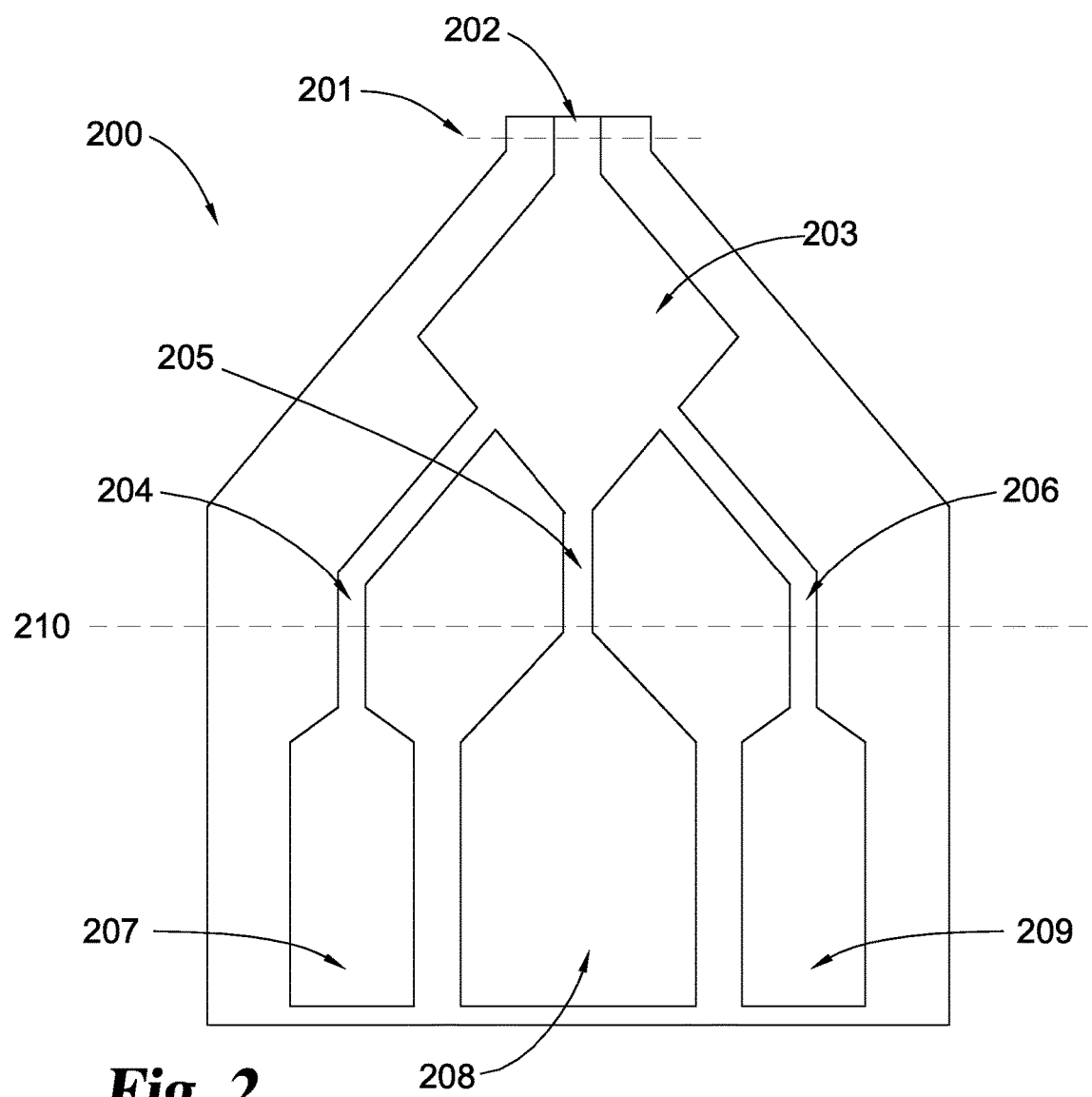
FIG. 2 is a plan view of another embodiment of the present disclosure.

FIG. 2 shows a plan view of another embodiment of the present disclosure. In this embodiment, a cryogenic bag is generally designated 200. Cryogenic bag 200 may be cut along dotted line 201, for example by a pair of scissors, to remove a composition, for example a putty, that is prepared in mixing compartment 203 through channel 202. Storage compartments 207, 208 and 209 may be in fluid communication to mixing compartment 203 through channels 204, 205 and 206. A clamp may be placed over, and/or a re-sealable closure such as a Ziploc® seal may be installed on line 210 or at another suitable location. The contents of compartments 207, 208 and/or 209 may be any of those materials disclosed herein, preferably including a cellular composition, a solids composition, and in some embodiments also a carrier composition, separately stored as described herein.

Figure 3:
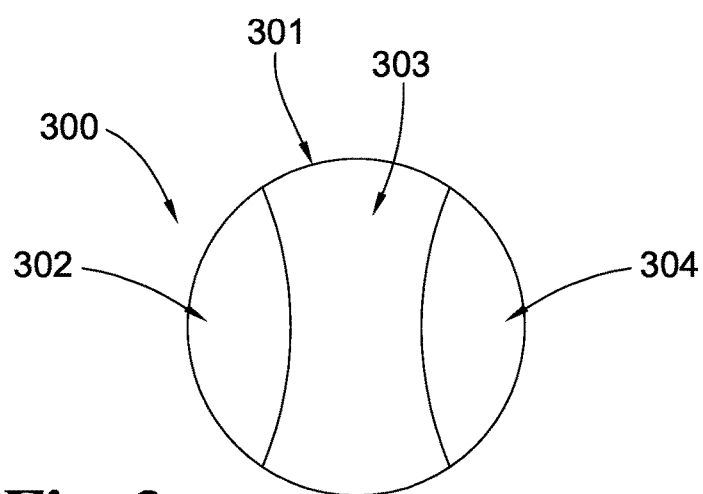
FIG. 3 is a top plan view of yet another embodiment of the present disclosure.

FIG. 3 shows a top plan view of another embodiment of the present disclosure. In this embodiment, a cryogenic bag is generally designated 300 is formed by a plastic wall 301 to provide storage compartments 302, 303, and 304. Compositions may be placed in storage compartments 302, 303, and/or 304 by, for example, pipetting compositions into the storage compartments. The cryogenic bag may then be sealed and the compositions frozen by, for example, placing the bag and its contents in a cryogenic liquid. The compositions may be held in the storage compartments by gravity (e.g. with the openings of the compartments positioned above the top surface of the respective contents of the compartments). Upon warming, the bag may be inverted and the compositions mixed together inside cryogenic bag 300. The contents of compartments 302, 303 and/or 304 may be any of those materials disclosed herein, preferably including a cellular composition, a solids composition, and in some embodiments also a carrier composition, separately stored as described herein.

In one embodiment, a cryogenic bag of the present disclosure can hold a total volume of less than or equal to about 200 mL, about 100 mL, 50 mL, and/or about 25 mL. In another embodiment, a cryogenic bag of the present disclosure can hold a total volume of about 1 mL to about 50 mL, and/or about 1 mL to about 20 mL. In another embodiment, one or more storage compartments may each hold a volume of about 1 mL to about 20 mL.

A solid material to be included herein can be any of a variety of solid materials (typically insoluble in water) that can be usefully combined with cells. In preferred embodiments, the solid material will be or will include a porous matrix composition, for example a natural or synthetic polymeric material, a porous inorganic material such as a ceramic or glass material, or combinations thereof. In certain embodiments, the porous matrix material will be or will comprise an ECM tissue. When used, the ECM tissue will typically be a collagenous material. For example, suitable collagenous ECM materials include those comprising submucosa, renal capsule membrane, dermal collagen, dura mater, pericardium, fascia lata, serosa, peritoneum or basement membrane layers, including liver basement membrane. These or other ECM materials that occur as connective tissue sheets in soft tissue of the patient, and that can be isolated as such sheets, are preferred. Suitable submucosa-containing ECM materials for these purposes include, for instance, ECMs including intestinal submucosa (e.g., small intestinal submucosa), stomach submucosa, urinary bladder submucosa, and uterine submucosa. Collagenous ECM materials comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567, each of which is hereby incorporated in its entirety herein.

Submucosa-containing or other ECM tissue when used in the invention is preferably highly purified, for example, as described in U.S. Pat. No. 6,206,931 to Cook et al., which is hereby incorporated in its entirety herein. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931, which is hereby incorporated in its entirety herein, may be characteristic of any ECM tissue used in the present invention.

In some aspects, a typical layer thickness for an isolated submucosa or other ECM connective tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue when used desirably retains a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction. When processed to a particulate ECM tissue, at least some of this structural microarchitecture can remain in the individual particles.

The ECM tissue is advantageously a remodelable material that promotes the formation of new tissue in the patient as the implanted or applied ECM tissue is resorbed. The particulate ECM material can exhibit angiogenic properties and promote cellular invasion and ingrowth.

The particulate ECM tissue material may include one or more bioactive factors. Suitable bioactive agents may include one or more bioactive factors native to the source tissue for the ECM tissue. For example, a submucosa or other ECM tissue material may retain one or more native growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials may retain other native bioactive factors such as but not limited to proteins, glycoproteins, proteoglycans, and glycosaminoglycans. For example, ECM materials may include native heparin, heparin sulfate, hyaluronic acid, fibronectin, cytokines, and the like. Thus, generally speaking, a particulate submucosal or other particulate ECM tissue material may retain one or more bioactive components that induce, directly or indirectly, a cellular response such as a change in cell morphology, proliferation, growth, and protein or gene expression.

Particulate ECM materials used in the invention will typically include abundant collagen, most commonly being constituted at least about 80% by weight collagen on a dry weight basis. Naturally-derived ECM materials typically include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

The ECM material will typically be porous. The porosity of the ECM material can be controlled to some extent by processing techniques. For example the porosity of the ECM material can be reduced by drying the material under compression, for example by drying a starting material ECM layer prior to comminution, or the formed particulate, under compression. On the other hand, an relatively higher porosity ECM material can be prepared by drying the ECM material by lyophilization, for example by freeze drying or evaporative cooling techniques. Such porosity-reducing or porosity-maintaining or porosity-increasing techniques can be used to provide the particulate ECM material with a desired level of porosity for a particular application.

The submucosa-containing or other ECM material used in the present invention may also exhibit an angiogenic character and thus be effective to induce angiogenesis in a host treated with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g., heparin, antibiotics, anti-inflammatory agents, thrombus-promoting substances such as blood clotting factors, e.g., thrombin, fibrinogen, and the like, and others. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure, or during or after application of the material to the patient. Other non-native components that may be added include, but are not limited to, ceramic compositions, solid compositions, echogenic compositions, metals, and/or other compositions visible under x-ray visualization and/or fluoroscopy.

The ECM material used in aspects herein can be xenogenic, allogenic, or autologous relative to the treated patient. As well, additional materials incorporated in the compositions herein may also be animal-derived, and may be xenogenic, allogenic, or autologous relative to the treated patient. In certain aspects, a human patient will be treated with a composition comprising a xenogenic particulate ECM tissue (e.g., porcine-, bovine- or ovine-derived) that is combined in the composition with a human material(s) that is/are autologous or allogenic relative to the human patient.

When used, a particulate ECM tissue can be formed by cutting, tearing, grinding or otherwise, comminuting a larger, decellularized ECM connective tissue layer material as described above to form a particulate. For example, cryogrinding or milling operations can be used to form the particulate ECM tissue material from larger layer. These comminution processes can form random fragments of the ECM tissue layer. The particle size of the particulate ECM tissue can vary. In preferred aspects, the average particle size of the particulate ECM tissue will be in the range of about 20 microns to about 500 microns, more preferably about 50 microns to about 400 microns. The particulate ECM tissue incorporated into compositions of this disclosure can be an unfractionated particle population prepared by the comminution, or can be a fraction of the particle population prepared by the comminution. Such fractions can for example be obtained by conventional techniques such as screening or sieving.

As-prepared cellularized compositions of the invention may include a (at least one) sugar. In the cryogenic product, this sugar or sugars may be included in a cellular composition, in a porous matrix composition, in a carrier composition, or any combination thereof. The sugar may, for example, be a simple sugar such as fructose or glucose, or another sugar such as sucrose. These or other monosaccharide or disaccharide sugars are preferred, and fructose is particularly preferred. Such sugars are generally available commercially (including United States Pharmacopeia (USP) grade) as powders, and can be used in that form herein. Fructose is preferred for inclusion in or as a sugar component of the as-prepared cellularized compositions herein, and can constitute at least 50% of the sugar, at least 75% of the sugar, at least 90% of the sugar, at least 99% of the sugar, or all or essentially all of the sugar included in the as-prepared cellularized composition.

The incorporation of a sugar such as can improve the physical characteristics of a cellularized composition prepared as described herein. For example, superior shape retaining but formable putties can result when using the sugar or sugars in combination of a porous matrix material such as a particulate ECM tissue.

A variety of aqueous media, liquid carriers, and/or other materials including biocompatible liquids can be included in the as-prepared cellularized compositions disclosed herein. Examples of suitable aqueous mediums include but are not limited to water, saline, or other pharmaceutically acceptable liquids.

Putty compositions of the invention can include appropriate ratios of the solid material (e.g. particulate ECM tissue or other porous matrix material) and liquid to one another, and appropriate overall levels of these components in the composition, in order to provide the desired physical properties to the composition (e.g., that of a shape retaining putty). One preferred form of putty composition is shape retaining, but formable to a new shape by application of force. Still further, the preferred putty or other composition can exhibit cohesiveness such that upon deformation the composition does not form cracks but instead flows to a new shape while retaining an intact continuous material matrix. For solid components such as the porous matrix (e.g ECM particulate) incorporated into the as-prepared composition, unless indicated otherwise, the ratios and percentages expressed herein are expressed on a dry weight basis.

In certain aspects, the weight ratio of liquid to total solids in an as-prepared putty or other composition herein is about 3:1 to about 7:1, or about 4:1. Additionally or alternatively, the weight ratio of liquid to porous matrix composition (e.g., particulate ECM tissue) in the putty or other composition is about 5:1 to about 10:1, or about 6:1. Additionally or alternatively, when one or more sugars is included, the weight ratio of porous matrix (e.g., particulate ECM tissue) to sugar (expressed as total sugars when more than one is included) in the putty can be about 10:1 to about 1:1, about 5:1 to about 1:1, about 3:1 to about 1:1, or about 2:1.

In respect of overall composition levels of these components, the putty or other as-prepared cellularized composition can be constituted of about 70% to about 90% by weight of liquid, or about 75% to about 85% of liquid, or about 80% of liquid. Additionally or alternatively, the putty or other composition can be constituted from about 5% to about 20% by weight of the particulate ECM tissue or other porous matrix, or about 10% to about 15% of the particulate ECM tissue or other porous matrix. Additionally or alternatively, the putty or other composition can be constituted from about 2% to about 10% by weight of one or more sugars, or about 5% to about 8%, or about 6% to about 8% of one or more sugars, in certain embodiments.

Cells suitable use in embodiments of the present invention include, but are not limited to stem cells. Such stem cells may be derived from human sources, including, but not limited to human umbilical cord blood, peripheral blood, and/or bone marrow. These sources may be allogenic, homologous or autologous. Sources of stem cells may be embryonic, or adult stem cells. In certain embodiments, stems cells are pluripotent and/or undifferentiated.

In further embodiments, a putty or other as-prepared composition as described herein is applied to a patient, such as a human or veterinary patient, for instance to treat diseased and/or damaged tissue. The composition may be applied by any suitable technique including, for example, injecting, spreading, infusing, filling, compressing, packing and/or engrafting. A diseased or damaged tissue to be treated may be any of a variety of such tissues, including soft and hard tissues such as skin, muscle, body wall tissue, connective tissue, ligaments, tendons, bone, and others. Illustratively, in some forms the composition can be forced into contact with tissue surfaces so as to conform to those tissues and promote repair, which repair may include the development of new tissue of the patient. In certain preferred treatments, the composition is applied to an open cutaneous wound of a patient, for example a cutaneous ulcer such as a diabetic ulcer, a burn, or other partial or full-thickness cutaneous wound.

In certain embodiments, a cryogenic bag or cryobag or other cryogenic container is used for transportation and/or storage of materials used to prepare compositions of the present disclosure. Having one or more compositions in a single, sterile cryogenic bag for transportation and/or storage may facilitate ease of use and application of compositions to a subject for treatment. In one embodiment, a cryogenic bag has one or more storage compartments for compositions, for example as described hereinabove. Additionally or alternatively, the cryogenic bag can have one or more mixing compartments, for example as described hereinabove.

Cryogenic bags use in embodiments of the present disclosure may be constructed out of any suitable material including, but not limited to plastic. In one embodiment, the plastic used comprises poly ethyl vinyl acetate or polyvinyl chloride. In one embodiment, the cryogenic bag may comprise visible indicia representing volumetric graduations on the cryogenic bag. Cryogenic bags of the present disclosure may comprise one, two, three, or more storage compartments and one, two, three, or more mixing compartments.

Cryogenic bags of the present disclosure may be formed by heat welding, injection molding, and/or any other suitable manufacturing technique for manipulating and/or forming materials. In one embodiment, heat welding is used to join two pieces of polymeric material to form a cryogenic bag comprising one or more storage compartments, one or more mixing compartments, and/or may also comprise one or more channels for fluid communication between one or more storage compartments and/or one or more mixing compartments. The one or more channels may be formed from the same material as the cryogenic bag is constructed from, and/or the channels may be reinforced and/or hardened. In certain embodiments, the storage compartments of the cryogenic bag, in a sealed form, are in fluid communication with one another, but the compositions remain unmixed and within their respective compartments by gravitational force. Once compositions have been placed in their respective compartments in the cryogenic bag, the bag may be sealed by, for example, heat welding.

Compositions to be placed in one or more storage compartments may comprise a cryoprotectant. Typically the cellular composition will comprise a cryoprotectant and/or will comprise an aqueous medium. Cryoprotectants suitable for use include, but are not limited to dimethyl sulfoxide; alcohols; glycols including but not limited to ethylene glycol, propylene glycol, propylene glycol, 2-methyl-2,4-pentanediol (MPD) and/or glycerine; and/or sugars including but not limited to sucrose.

In still other embodiments, separate compositions in a cryogenic bag need not be segregated by separate storage compartments. In one embodiment, a first composition is placed in a cryogenic bag and frozen. A second composition is then placed the cryogenic bag adjacent to the now frozen composition and the second composition is then frozen. This provides a cryogenic bag where the first and second compositions come into minimal contact with each other and/or are generally non-mixable with one another under cryogenic storage conditions (e.g. provided as discrete, frozen material masses). In still other embodiments, a third composition is placed in the cryogenic bag with the first and second now frozen compositions. The third composition is then frozen along with the first and second compositions already in a solid state, to form a third discrete solid mass within the bag.

In certain embodiments, the porous matrix or other material, typically a solid material, can be one that decreases the viability of the cells when in contact with the cells during cryogenic processing, such as during freezing of the cellular composition. Such materials are referred to herein as cryodamage sensitizing materials.

Compositions may be placed into a cryogenic bag of the present disclosure by any suitable means, including, but not limited to transferring compositions by pipette, cannula, pouring, or placing the compositions in a cryogenic bag. In one embodiment, the one or more storage and/or mixing compartments may have one or more ports capable of fluid communication with an external storage or transfer vessel for the purpose of, for example, filling the one or more storage compartments. In yet another embodiment, a clamp or other device may be used to position one or more compositions before, during, and/or after freezing the one or more compositions placed in a cryogenic bag of the present disclosure.

In some embodiments, a cryogenic product as described herein can be removed from a cryogenic storage device. The cryogenic bag can be warmed, e.g., to room temperature, for example by placing the cryogenic bag in contact with atmosphere or another warmer fluid such as a liquid. After the contents of the bag have been sufficiently warmed to be flowable, the bag can be inverted to allow gravity drain of the contents of the separate compartments through their respective compartment openings and into a mixing compartment. The external walls of the cryogenic bag can then be manipulated (e.g., kneaded) to mix the contents of the bag to prepare a cellularized composition. This mixing is preferably conducted while the cryogenic bag retains its sealed condition. After preparation of the cellularized composition is complete, the seal of the bag can be broken, and the cellularized composition removed and administered to the patient. In certain aspects, the sealed cryogenic bag includes a tapered portion, and a tip region of the tapered portion can be cut away to prepare an opening through which the as-prepared cellularized composition can be forced either for direct administration to patient tissue or for transfer to another container or delivery device.

To promote a further understanding of embodiments disclosed herein and their features and advantages, the following specific Examples are provided. It will be understood that these examples are illustrative, and not limiting, in nature.

EXAMPLE 1

Preparation of a Cryogenic Bag Comprising an ECM

Materials and Methods:

A sealed cryogenic bag with three storage compartments and one mixing compartment is prepared by placing a composition comprising an ECM in one storage compartment of the cryogenic bag. A composition comprising water (e.g., media, or a salt solution) is placed in the second compartment of the cryogenic bag. A composition comprising mesenchymal stem cells is placed in the third storage compartment of the cryogenic bag. The compartments each have an opening for introduction of the respective materials and those openings are left unsealed and fluidly communicating with the mixing compartment. The cryogenic bag is purged with an inert atmosphere such as nitrogen, argon, and/or carbon dioxide and sealed by heat welding. The cryogenic bag is cooled to cryogenic temperatures by placing the bag into a cryogenic storage compartment. During these operations, the bag is maintained in an upright position with the openings occurring at the upper ends of the first, second and third compartments, to keep the contents of the respective compartments from mixing with one another.

EXAMPLE 2

Preparation of a Putty in a Cryogenic Bag Comprising an ECM

Materials and Methods:

The cryogenic bag of EXAMPLE 1 is removed from a cryogenic storage compartment and allowed to slowly warm to room temperature by placing the bag in contact with atmosphere at room temperature.

Alternatively, the cryogenic bag of EXAMPLE 1 is removed from a cryogenic storage compartment and allowed or caused to rapidly warm to about 37° C.

After the cryogenic bag has warmed to room temperature or about 37° C., the bag is inverted sufficiently to transfer the compositions from the first, second and third compartments into the mixing compartment of the cryogenic bag. The contents of the mixing compartment are then kneaded gently by exerting pressure on the flexible walls of the bag to affect mixing of the three compositions in the mixing compartment, e.g., to form a putty. After mixing, the top of the cryogenic bag is cut off to create a dispensing opening and the as-prepared cellularized composition is dispensed from the bag through the dispensing opening.

The use of the terms "a" and "an" and "the" and similar referents in the context of describing the invention especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A cryogenic product useful for the preparation of a cellularized matrix composition, comprising:
    a cryogenic bag defining a sealed internal volume;
    a cryogenically preserved cellular composition received within a first compartment within said internal volume, wherein said first compartment defines a first opening positioned above an upper surface of said cellular composition;
    a water-insoluble, particulate porous matrix material received within a second compartment within said internal volume, wherein said second compartment defines a second opening positioned above an upper surface of said water-insoluble, particulate porous matrix material; and
    wherein said first opening and second opening each open to a third compartment within said internal volume for mixing said cellular composition with said water-insoluble, particulate porous matrix material, said third compartment being positioned above said first compartment and said second compartment, and said third compartment having a flexible wall that capable of mixing said cellular composition and said water-insoluble, particulate porous matrix material after thawing of said cryogenic bag after transferring said cellular composition through said first opening into said third compartment after transferring said water-insoluble particulate porous matrix material through said second opening into said third compartment.

2. The cryogenic product of claim 1, also comprising a frozen liquid carrier composition received within a fourth compartment within said internal volume, said fourth compartment also defining an opening to said third compartment.

3. The cryogenic product of claim 1, wherein said water insoluble, particulate porous matrix material comprises a natural or synthetic polymeric material.

4. The cryogenic product of claim 1, wherein said water insoluble, particulate porous matrix material comprises collagen.

5. The cryogenic product of claim 1, wherein said porous matrix composition comprises an extracellular matrix.

6. The cryogenic product of claim 5, wherein said extracellular matrix comprises submucosal tissue.

7. The cryogenic product of claim 1, wherein said first opening and/or said second opening has a maximum width smaller than a maximum width of the first compartment.

8. A method for preparing a cellularized matrix composition, comprising:

thawing the cryogenic product of claim 1;

transferring the cellular composition from the first compartment to the third compartment;

transferring the water-insoluble, particulate porous matrix material from the second compartment to the third compartment; and mixing the cellular composition with the water-insoluble, particulate porous matrix material in the third compartment to form a cellularized composition.

9. The method of claim 8, wherein said transferring steps comprise inverting the cryogenic product so as to cause the cellular composition and solid composition to gravity flow into said third compartment.

10. The method of claim 8, further comprising disrupting the seal of said sealed internal volume, and removing said cellularized composition from said internal volume.

11. The method of claim 8, wherein said mixing comprises manipulating a flexible wall of said cryogenic bag so as to mix the cellular composition and solid composition in said third compartment.

12. The method of claim 11, wherein said manipulating is performed prior to disrupting the seal of said sealed internal volume.

13. The product of claim 1, wherein said first compartment and second compartment are formed by one or more compression elements external of said sealed internal volume and compressing regions of said storage container.

14. The product of claim 13, wherein said one or more compression elements are manipulable to release compression on said regions of said storage container so as to eliminate said first and second compartments.

15. The product of claim 14, wherein said one or compression elements comprise one or more clamps.

16. The product of claim 1, wherein said porous matrix material includes an extracellular matrix material.

17. The product of claim 1, wherein the cellularized matrix composition prepared is a putty.

* * * * *